United States Patent

Johnson

Patent Number: 5,833,457
Date of Patent: Nov. 10, 1998

[54] ENDODONTIC OBTURATOR

[75] Inventor: William B. Johnson, Tulsa, Okla.

[73] Assignee: Dentsply International Inc., York, Pa.

[21] Appl. No.: 826,831

[22] Filed: Apr. 8, 1997

Related U.S. Application Data

[60] Provisional application No. 60/031,029, Nov. 18, 1996.
[51] Int. Cl.⁶ ....................................................... A61G 5/02
[52] U.S. Cl. .............................. 433/81; 433/102; 433/224
[58] Field of Search ................................ 433/81, 83, 102, 433/224

[56] References Cited

U.S. PATENT DOCUMENTS

| | | | |
|---|---|---|---|
| 1,757,595 | 5/1930 | Siegel | 433/224 |
| 4,019,254 | 4/1977 | Malmin | 433/102 |
| 4,758,156 | 7/1988 | Johnson | 433/81 |
| 4,894,011 | 1/1990 | Johnson | 433/81 |
| 5,118,297 | 6/1992 | Johnson | 433/224 |
| 5,302,129 | 4/1994 | Heath et al. | 433/81 |

*Primary Examiner*—John J. Wilson
*Attorney, Agent, or Firm*—James B. Bieber

[57] ABSTRACT

An obturator for use in filling an endodontically prepared root canal in a tooth formed as an elongated body having a handle portion and a shaft, the handle portion being configured for grasping by a practitioner whereby the shaft may be inserted into a root canal, the shaft tapering from the handle to the shaft distal end, the shaft having an exterior surface having a generally linear groove therein extending from near the handle to the shaft distal end, or at least adjacent the shaft distal end, the groove providing: (a) a channel for flow of excess filler material as the shaft is positioned into a prepared root canal; (b) increased flexibility of the shaft, and (c) a passageway that will accept a slender, tapered metallic retrieval tool, such as a typical endodontic file, to assist in the removal of the shaft from a root canal.

11 Claims, 3 Drawing Sheets

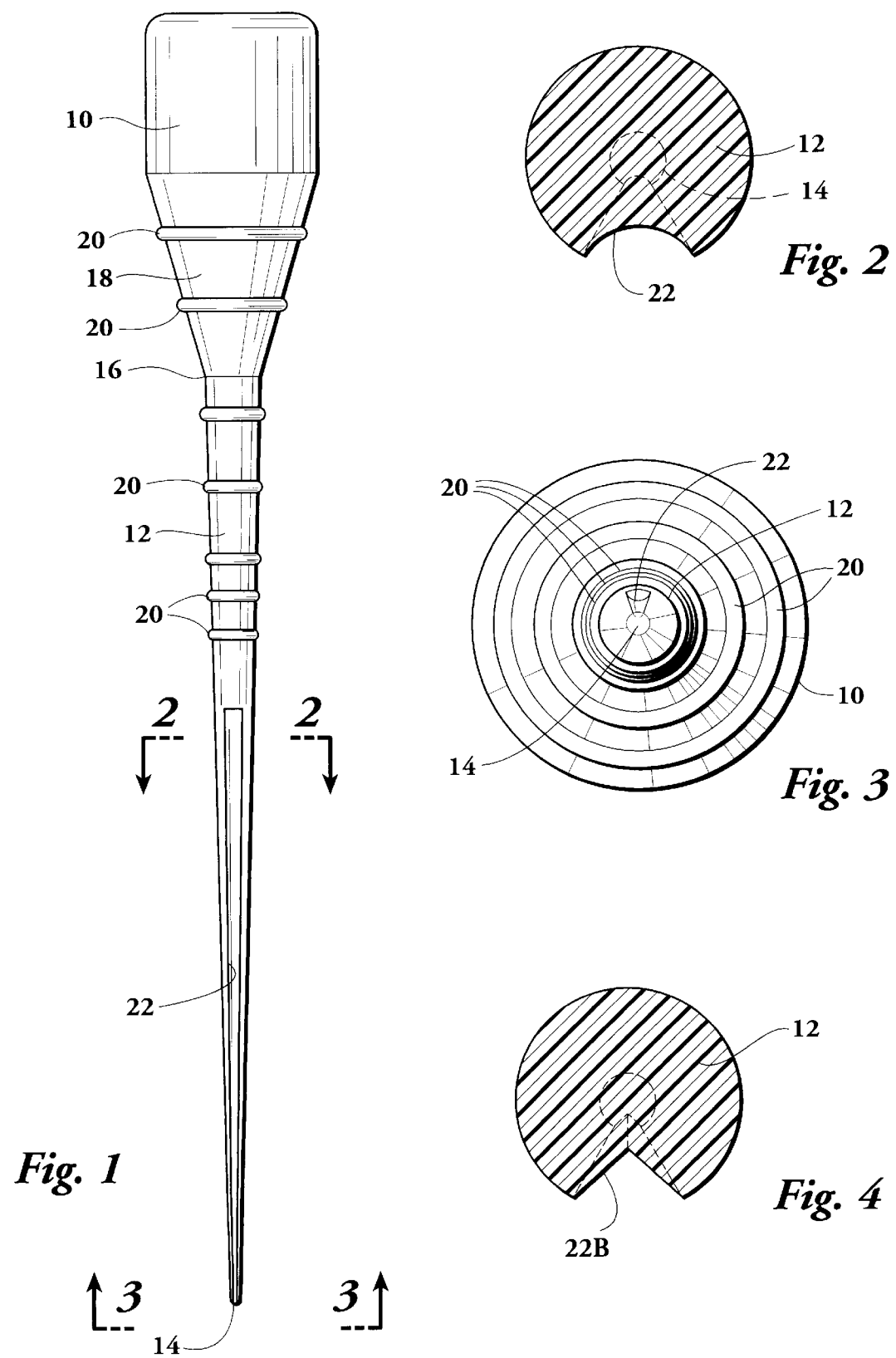

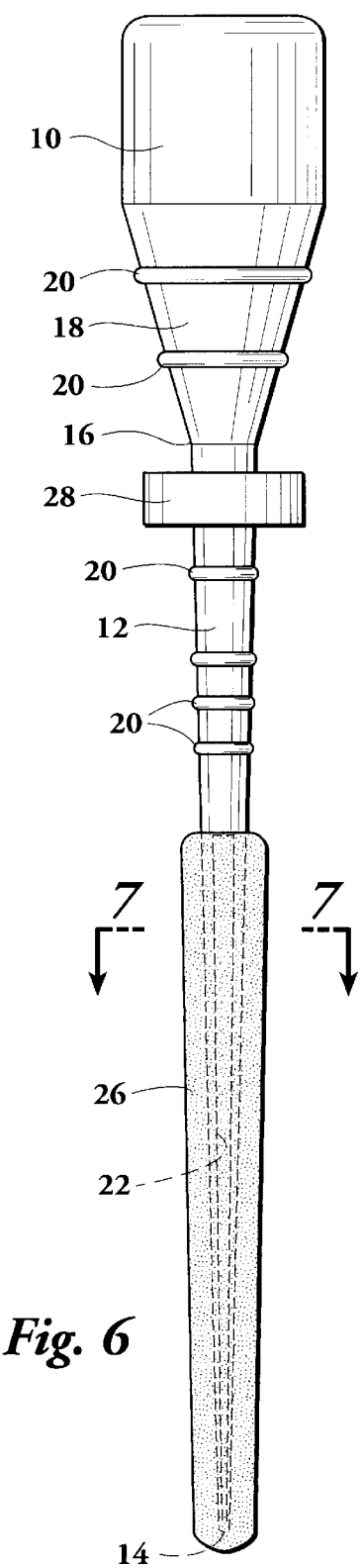
*Fig. 6*
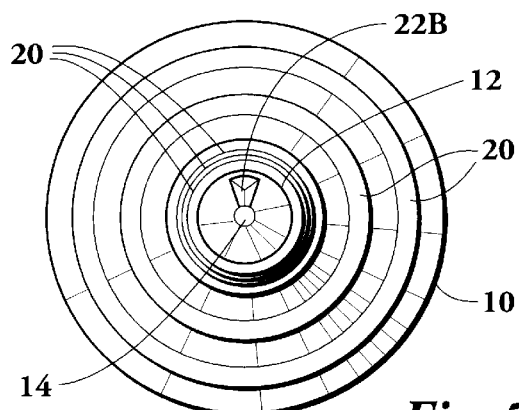
*Fig. 5*
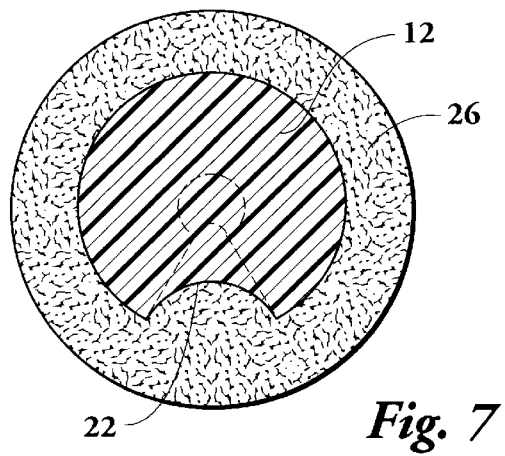
*Fig. 7*
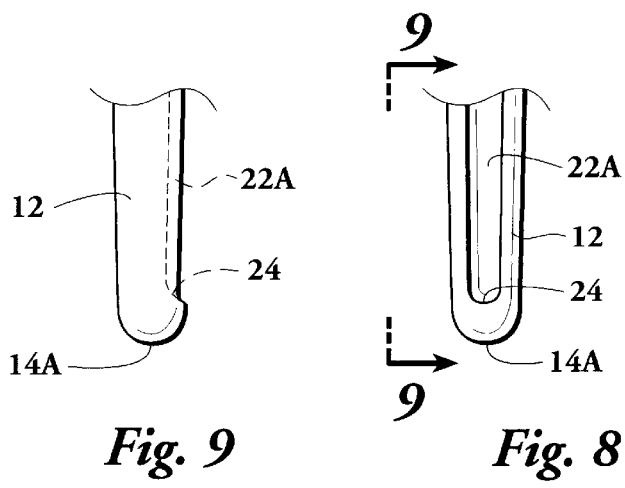
*Fig. 9*   *Fig. 8*

ENDODONTIC OBTURATOR

CROSS-REFERENCE TO RELATED APPLICATIONS

This application claims the benefit of and incorporates by reference prior filed Provisional Application No. 60/031,029 filed Nov. 18, 1996 entitled "Improved Endodontic Obturator".

CROSS-REFERENCE TO MICROFICHE APPENDIX

This application is not related to any microfiche appendix.

BACKGROUND OF THE INVENTION

Until about 1987 the most common technique for filling an endodontically prepared root canal of a tooth employed the steps of applying filler material (usually gutta percha) by means of an instrument called a "condenser" that includes a small diameter, usually straight portion with a blunt end that is frequently inserted into a root canal. Small quantities of gutta percha or other filler material can be carried by a condenser and the condenser then used to exert a compacting force to urge the gutta percha to fill the root canal. This procedure is time consuming and often does not result in adequately filling a root canal of an endodontically prepared tooth.

U.S. Pat. No. 4,758,156, applied for in 1987 and issued in 1988, disclosed a unique tool for applying filler material to an endodontically prepared root canal. The tool is in the form of an elongated obturator having a shaft portion for laterally expanding and compacting filler material as the obturator and filler material are conjointly inserted into a root canal.

U.S. Pat. No. 4,894,011, applied for in 1988 and issued in 1990, disclosed further improvements to this basic concept. One of the improvements illustrated and described in U.S. Pat. No. 4,894,011, in FIGS. 7 and 13 thereof, is the concept of placing a spiral groove or spiral grooves in the exterior surface of the obturator for the purpose of augmenting the retention of filler material. Further, this patent points out that by the use of spiral grooves the flexibility of the shaft is improved and by rotating the obturator in a reverse direction the obturator could be removed after insertion into a root canal, the reverse rotation serving to retain the filler material in the canal.

U.S. Pat. No. 5,118,297, filed Jan. 9, 1991 and issued Jun. 2, 1992, discloses even further important advancements in endodontic obturators. This patent provides an endodontic obturator particularly adaptable to be formed of plastic and includes the important concept of gutta percha or other filler material being formed on the obturator in a way such that it can be heated, by a flame of a burner or in an oven, to assist in conveying filler material into a root canal.

The invention disclosed herein is an improvement in an endodontic obturator of the type illustrated and described in U.S. Pat. No. 5,118,297.

The patents discussed herein above, that is, U.S. Pat. Nos. 4,758,156; 4,894,011 and 5,118,297 are each incorporated by reference as fully as if the text and drawings were repeated herein.

BRIEF SUMMARY OF THE INVENTION

An improved obturator for use in filling an endodontically prepared root canal is disclosed. The improved obturator includes an elongated slender body having a proximal end and a distal end. The body has a handle portion at the proximal end, the handle portion being in the form of an enlarged diameter portion of configuration and dimension to be manipulated by the thumb and forefinger of a practitioner for use in filling a root canal.

Extending from the handle portion is a shaft dimensioned to be received in an endodontically prepared root canal, the shaft preferably being tapered and having a surface adapted to receive filler material thereon.

Formed in the shaft portion is one or more grooves that extend from adjacent the handle portion to adjacent the distal end of the shaft. In one embodiment the groove can extend all the way to the distal end of the shaft while in another embodiment the groove extends to immediately adjacent the distal end so that the distal end has an uninterrupted circumferential surface in a plane drawn perpendicular to the longitudinal axis of the shaft. This rounded terminal surface that may be termed "a bullet nose" end configuration.

The groove formed in the external surface of the shaft serves at least three important functions. First, the groove permits a passageway for the flow of excess filler material upwardly out of the depths of a root canal during the obturation process, that is, any excess filler material can freely move out of the root canal thereby making it easier for the practitioner to insert the distal portion all the way to the root canal apex. A second advantage of the provision of one or more grooves in the exterior surface of the obturator shaft is that flexibility of the shaft is increased. Root canals are seldom straight requiring the obturator to bend and flex as it is inserted into a root canal during the obturation process, the increased flexibility imparted by the provision of one or more grooves improves the performance of the obturator.

A third and significant advantage obtained by the provision of one or more grooves in the exterior surface of the shaft of the obturator is that a re-entry area is provided. A specific and important example of the use which may be made of the re-entry area afforded by the groove is that it permits an instrument, such as a file, and particularly such as a file having a barbed exterior surface, to be inserted into a root canal following the groove formed in the obturator shaft, providing means whereby the obturator can be extracted from a root canal.

One of the serious problems with the use of obturators is that they interfere with reopening the root canal in the event an infection develops or for other reasons it is important to have access to a root canal after it has been obturated. In the past, extracting obturators has been a serious problem, however, with the provision of this invention, the obturator body can be effectively extracted. The extraction capability afforded by this invention is particularly important when it is fully appreciated that a file or other slender metallic extraction instruments inserted into a root canal following the groove formed in the obturator body can extend to substantially the full length of the shaft to engage the shaft along its full length and permit it to be extracted. It is easily seen that if an extractor engages only a portion of the shaft that is in the direction away from the distal end that extractions can frequently result in severing the shaft leaving the lowermost portion, that is the portion adjacent the tooth apical area, in the tooth. Putting it another way, the most difficult part of an obturator body to extract is the most distal portion which is the portion having the smallest cross-sectional area and therefore the area easiest to sever during an extraction process. By this invention, an extraction tool can be inserted to substantially the full depth of the root canal along the groove provided in the shaft to substantially increase the possibility that the full length of the shaft can be removed from a root canal.

In one embodiment of the invention the obturator includes filler material formed on the shaft portion so as to expedite filling a root canal.

A better and more complete understanding of the invention will be obtained from the following description of the preferred embodiments taken in conjunction with the attached drawings.

DESCRIPTION OF THE DRAWINGS

FIG. 1 is an elevational enlarged view of an endodontic obturator that includes the improvements of this invention.

FIG. 2 is a greatly enlarged cross-sectional view as taken along the line 2—2 of FIG. 1 showing one configuration of a groove as provided in the external surface of the shaft portion of an obturator.

FIG. 3 is an enlarged end view as taken along the line 3—3 of FIG. 1.

FIG. 4 is a cross-sectional view as shown in FIG. 2 but showing an alternate design of the groove formed in the external surface of the shaft portion of the obturator body.

FIG. 5 is a view as shown in FIG. 3 but showing the appearance of an obturator body as seen from the distal end when a groove having straight sidewalls as shown in FIG. 4 is employed.

FIG. 6 is an elevational view of an obturator body, such as one shown in FIG. 1, but including filler material adhered to the shaft portion. The obturator of FIG. 6 may be supplied directly by a manufacturer with the filler material formed thereon, the material being subject to being heated in a flame or in an oven to soften the filler material before it is inserted into a root canal. FIG. 6 includes a sliding stopper or washer on the obturator body shaft.

FIG. 7 is an enlarged cross-sectional view as taken along the line 7—7 of FIG. 6 showing the obturator body in cross-section having a groove with an arcuate cross-sectional configuration and showing the filler material as formed on the obturator shaft portion.

FIG. 8 is a fragmentary elevational view of the distal end portion of an obturator body shaft portion showing a groove formed in the external surface of the shaft portion and showing the arrangement wherein the groove terminates just short of the shaft distal end leaving a "bullet nose" end configuration.

FIG. 9 is an elevational view of the obturator shaft distal end portion as taken along the line 9—9 of FIG. 8.

DESCRIPTION OF THE PREFERRED EMBODIMENTS

Figure 11:
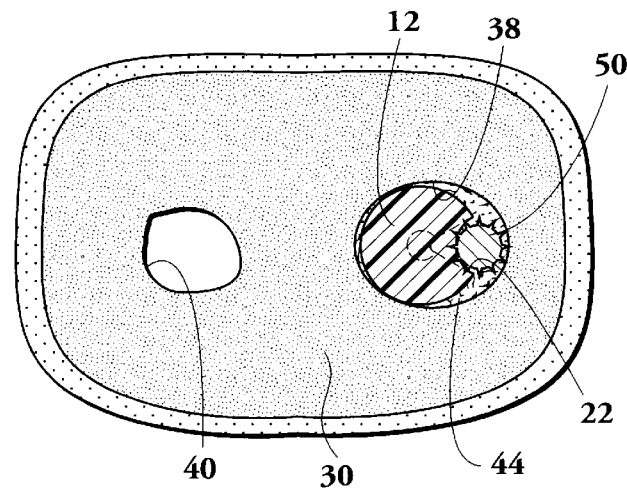
FIG. 11 is a cross-sectional view taken along the line 11—11 of FIG. 10 showing the shaft portion of an obturator of this invention having a groove in the exterior surface and showing a retrieval tool, such as an endodontic file, inserted into the root canal in the area provided by the groove to assist in removing the shaft portion from the root canal.

Referring to the drawings and first to FIG. 1, an enlarged elevational view of an embodiment of the improved endodontic obturator is shown. The obturator includes a proximal handle portion 10 dimensioned to be manipulated between the thumb and forefinger of the user. Integrally extending from handle portion 10 is a shaft portion 12 that terminates in a distal end 14. Shaft 12 is tapered and has an external surface adapted to receive an endodontic filler material, such as gutta percha, thereon. Shaft portion 12 tapers from the maximum diameter at junction 16 where the shaft meets a conical portion 18 of handle 10, the shaft tapering from a maximum diameter at junction 16 to a minimum diameter at distal end 14.

Integrally formed on shaft 18 are spaced apart length indicators 20 that are, as explained in U.S. Pat. No. 5,118,297, useful for indicating the distance that the shaft proximal end 14 has penetrated into a root canal so that the practitioner can, after the canal is filled with a filler material, insert the obturator and know that the distal end has penetrated to the depth as indicated by an indicator 20. Handle portion 18 has depth indicators that are useful when the obturator is employed in a tooth having an unusually long root canal.

Junction 16 is an external indication only of change in the shape of the tapered surface of shaft 12 and handle conical portion 18 and does not indicate a separation in the overall integral obturator.

The obturator described to this point is substantially identical to the obturator described in previously issued U.S. Pat. Nos. 4,894,011 and 5,118,297. A significant and important improvement is the provision of a groove 22 formed in the external surface of the obturator shaft portion 12. Groove 22 extends from an upper portion of shaft 12 to distal end 14. In the embodiment of FIG. 1 the groove extends completely to the end of shaft portion 14.

FIGS. 8 and 9 show the end portion of shaft 12 including the distal end and illustrates groove 22A as formed in the external surface of the shaft portion, the groove terminating short of the shaft distal end 14A. In the embodiment of FIGS. 8 and 9, groove 22A has a terminal point 24 that is slightly spaced above the shaft distal end 14A. This alternate embodiment permits end 14A to be defined by an uninterrupted circumferential surface and provides a "bullet nose" end configuration identified by the numeral 14A to distinguish the configurations of FIGS. 8 and 9 from that of FIG. 1. The bullet nose end 14A has an important advantage over the end configuration of FIG. 1, that is, by terminating groove 22A just short of the distal end permits the distal end to be uninterrupted, that is, providing a full circumferential surface. The bullet nose end configuration is less likely to engage or "hang up" on an irregularity in a root canal that would interfere with the complete advancement of the obturator to the root apex. Further, the terminus of a root canal at the apex of a tooth provides a potential point of entry of contaminants into the tooth. By employing an obturator having a circumferential end as seen in FIGS. 8 and 9, the obturator can more effectively close the apex end of the root canal and thereby more effectively guard against entry of contaminants into the canal after the endodontic procedure has been completed.

FIG. 2 shows a cross-section of the obturator shaft 12 and groove 20. In this figure, groove 22 is arcuate, however the cross-sectional shape of the groove can vary. For instance, FIG. 4 is an alternate embodiment wherein groove 22B has an angular cross-sectional configuration. The angle forming the walls of the groove can vary considerably from an acute to an obtuse angle. Not only can the cross-sectional shape of groove 22 vary but the depth can vary considerably. One important advantage of providing groove 22 in the shaft portion of the obturator is that it increases flexibility of the shaft. However, the groove has the contravailing characteristic of reducing the strength of the shaft. Therefore, the depth, shape and cross-sectional area of groove 22 must be selected as a compromise between preserving the required strength of the shaft and achieving the desired increase in flexibility of the shaft.

In addition to increased flexibility of the shaft portion, another significant advantage of the provision of groove 22 is that it allows for the escape of excess filler material as the obturator is inserted into a root canal having filler material therein. An important function of the obturator is to compact filler material in a root canal to eliminate, as much as possible, any voids and to cause the filler material to flow into lateral fissures that frequently characterize root canals. Therefore, it is important that the root canal be as full as possible of filler material as the obturator is inserted into the canal but, at the same time, it is important that provision be made for the escape of excess material. When the obturator is inserted into a root canal having filler material therein, the obturator should be positioned at its full depth into the canal with distal end 14 as close as practically possible to the root canal apex and therefore, any excess accumulation of filler material in the root canal can, by hydraulic action, interfere with positioning the obturator in the root canal in a tooth in some instances. With the provision of groove 22 any excess filler material can flow to the tooth surface and hydraulically resistance to positioning the obturator shaft portion in the root canal is alleviated.

FIG. 3 is an end view of the obturator showing the groove 22 extending to distal end 14. FIG. 5 shows an end view of an obturator having an angular groove 22B as shown in FIG. 4.

An important advancement of the state of endodontics has been the commercial availability of obturators having filler material formed thereon. FIGS. 6 and 7 show the obturator of FIG. 1 having filler material 26 formed thereon. Filler material 26 is typically gutta percha but may be other compounds which have the desirable characteristic to function as a root canal filler. The typical commercially available obturator has filler material 26 thereon which at ambient temperature is relatively rigid. Filler material 26 can be heated either over an open flame or in an oven to a temperature at which it become semi-molten before the obturator having the filler material thereon is inserted into a root canal.

FIG. 6 shows an elastomeric washer 28 that can be used for assistance in compacting a filler material into a root canal, as has been explained in the previously issued patents referred to hereinabove.

The provision of an improved endodontic obturator having a groove 22 has, in addition to the advantages previously mentioned, a highly important advantage compared to other obturators, that is, groove 22 provides a re-entry passageway into a root canal. If an endodontic procedure is unsuccessful, that is, if infection or other problems develop, it is sometimes desirable that further work be done within the root canal. For this reason it is important to be able to extract an obturator from a root canal. Heretofore, this has been a serious problem. If obturators are made of plastic, the preferred material with which the present invention is made, the obturator can be drilled out of the root canal. However, drilling is not easily accomplished in a root canal that is not straight. Therefore, it is highly desirable to be able to extract an obturator from a tooth. Groove 22 provides a passageway by which a practitioner can insert a dental file or other long, thin metal instrument having an irregular surface, particularly one having a barbed surface, to engage the plastic obturator and permit extraction of the obturator. Since groove 22 extends the full length of the obturator shaft, a file or other similar tool having the characteristics of being thin, flexible and strong, and with a surface that will adhere to plastic obturator shaft 12, can be inserted the full length of the obturator, thereby permitting the full obturator shaft to be extracted from a tooth. Whereas the upper portion of an obturator, being the larger diameter portion of the tapered shaft, can usually be grasped in some way and removed, a common problem is breaking off the obturator so that the lower portion remains in the root canal. By the provision of groove 22 an instrument can be extended to the apical end 14 of the obturator to permit its extraction.

Figure 10:
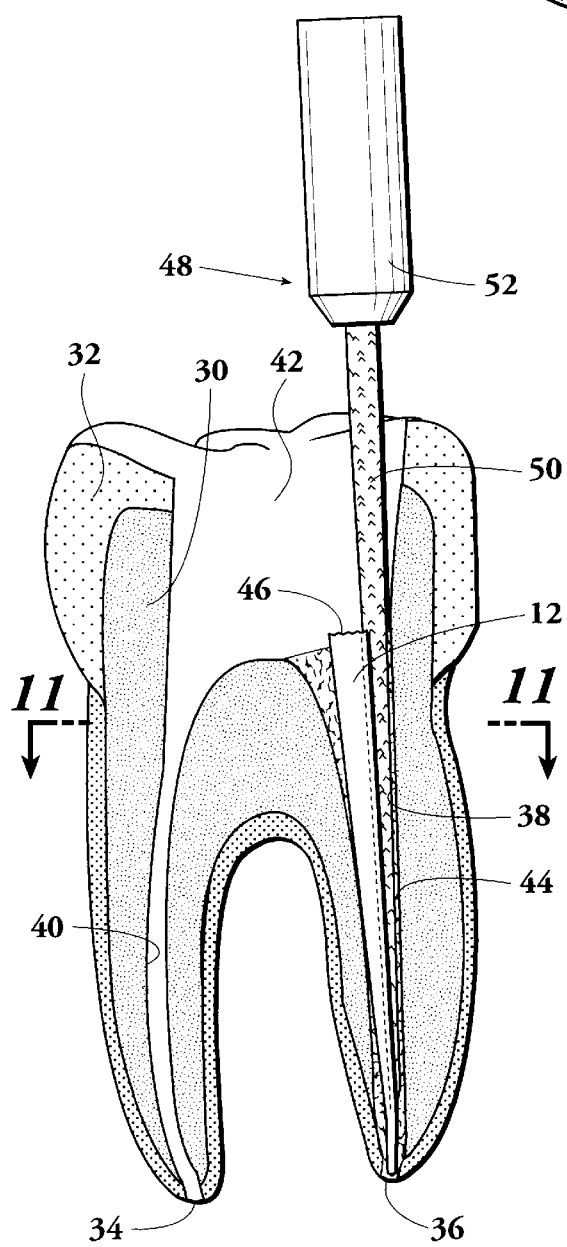
FIG. 10 is an elevational cross-sectional view of a typical bicuspid tooth showing a root canal having therein a shaft portion of an endodontic obturator of this invention as the shaft portion has been severed from the handle portion during the procedure for filling the root canal and showing the use of a retrieval tool (typically an endodontic file) that is inserted into the root canal along the groove formed in the exterior surface of the obturator to assist in removing the severed shaft portion from the root canal.

FIGS. 10 and 11 illustrate this important aspect of the improved obturator. A tooth 30 is shown in cross-section, the tooth being representative of a bicuspid with a coronal area 32 and root apexes 34 and 36. The tooth has a first root canal 38 and a second root canal 40. The first root canal 38 is shown as having been endodontically treated, that is, enlarged, shaped and cleaned by the use of dental files whereas the second root canal 40 is more typical of the appearance of the root canal prior to being endodontically treated. The tooth has a pulp cavity 42 that, after the enamel and dentine which normally covers the pulp cavity at the coronal area 32 has been removed, exposes root canals 38 and 40.

Positioned in root canal 38 is a shaft 12 of an endodontic obturator, such as the obturator of FIG. 1, the shaft having been inserted into root canal 30 in conjunction with filler material 44, such as gutta percha. Shaft 12 has been severed at 46 as is the procedure for the use of the obturator for filling a root canal. Tooth 30 is shown as the tooth would appear with first root canal 38 filled by the obturator and showing the circumstances under which, for one reason or another, the obturator shaft needs to be extracted from the root canal.

As has been previously stated, since the obturator shaft portion is preferably formed of plastic, it can be drilled out of the root canal 38 but such procedure is difficult because of the fact root canals are seldom straight and are usually of tapered shape. Therefore, it is highly desirable to be able to extract obturator shaft 12. For this purpose, an extraction tool, generally indicated by numeral 48 is employed. The extraction tool 48 has a metal shaft 50 and a handle portion 52, the handle being typically formed of plastic. Shaft 50 has an exterior surface that is irregular and may include barbs, grooves or the like. Extraction tool 48 can be conveniently provided in the form of an endodontic file that is used by practitioners to endodontically prepare a root canal. Such files typically have grooves that are configured to scrape the sides of a root canal when the file is withdrawn in the direction towards the coronal area, that is, out of the root canal.

FIGS. 10 and 11 show shaft 50 of the extraction tool 48 inserted into the root canal using the access provided by groove 22 that is formed in obturator shaft 12.

The irregular surface of shaft 50 tends to imbed into the plastic obturator shaft 12 so that upon outward pull relative to the tooth coronal area 32, using handle 52, the obturator shaft 12 can be extracted.

The provision of groove 22 in the shaft portion of the obturator allows a extraction tool or endodontic file, to be inserted substantially to the full length of the shaft as compared with an attempt to insert an endodontic file along a shaft that has no groove. Putting it another way, without the provision of groove 22 it is difficult to extend the shaft of an extraction tool or dental file to substantially the full length of an obturator shaft 12; however, with the provision of groove 22 the possibility of extending the extraction tool shaft to substantially the distal end of the filler shaft is substantially improved, thereby improving the possibility of successfully extracting the full length of an obturator shaft from a root canal.

In the embodiment of FIGS. 8 and 9 wherein the groove terminates a short space away from the obturator distal end, nevertheless, the groove extends substantially to the complete end of the obturator so as to permit its full extraction.

Groove 22 should preferably be linear or at least substantially linear. Groove 22 could be slightly helical and still function for the three important purposes enumerated herein, that is, groove 22 could curve for a fraction of a circumference around the external peripheral surface of obturator shaft 12, however a groove of more than about 180° around the shaft periphery is not desirable since it makes insertion of a file or other tool used for removal of the obturator more difficult. Therefore, it can be said that groove 22 should be "substantially linear", that is, preferably linear but could be non-linear to a limited degree and still accomplish the purposes and intentions of the invention. Groove 22 can not be, for its intended purpose, a spiraled groove such as illustrated in U.S. Pat. No. 4,894,011. While the spiraled groove of FIG. 7 of U.S. Pat. No. 4,894,011 adds flexibility, it adds substantially to the length of the groove to thereby interfere with the function of the groove to form a passageway for the escape of excess filler material and would make the insertion of a file or other retrieval tool impossible.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An obturator for use in filling an endodontically prepared root canal in a tooth, comprising:

an elongated body having a proximal handle portion and a distal shaft portion, the handle portion being configured for grasping by a practitioner whereby the shaft portion may be inserted in a root canal, the shaft portion tapering from said handle portion to a distal end, the shaft portion having an exterior surface having a generally linear groove therein extending from adjacent said handle portion to adjacent said distal end.

2. An improved obturator according to claim 1 wherein said groove is dimensioned to permit any excess liquid filler material within a root canal to flow by way of said groove from within the exterior of a root canal.

3. An endodontic obturator according to claim 1 wherein said shaft distal end is rounded to form a bullet nose and wherein said groove extends to adjacent but not through said bullet nose whereby said bullet nose is left at least substantially intact.

4. An endodontic obturator according to claim 1 wherein said groove is, in cross-sections taken perpendicular a shaft longitudinal axis, of generally V-shaped configuration.

5. An endodontic obturator according to claim 1 wherein said groove is, in cross-sections taken perpendicular a shaft longitudinal axis, of generally arcuate configuration.

6. An endodontic obturator according to claim 1 wherein said shaft portion has filler material formed thereon encompassing at least a substantial portion of said shaft and said groove.

7. An endodontic obturator according to claim 1 wherein said groove is configured and dimensioned to receive a slender, tapered metallic retrieval tool to augment removal of the shaft portion from a root canal.

8. An endodontic obturator according to claim 7 wherein said groove is configured and dimensioned to receive an endodontic file for assistance in removing the shaft portion from a root canal.

9. An improved obturator according to claim 1 wherein said shaft portion exterior surface is generally circular in cross-sections taken perpendicular to a shaft longitudinal axis.

10. An improved obturator according to claim 1 wherein at least said shaft portion is formed of plastic.

11. An improved obturator according to claim 1 wherein said body handle portion and said shaft portion are integral and formed of plastic.

* * * * *